(12) United States Patent
Schlaudraff et al.

(10) Patent No.: US 9,804,144 B2
(45) Date of Patent: Oct. 31, 2017

(54) METHOD FOR DEFINING A LASER MICRODISSECTION REGION, AND ASSOCIATED LASER MICRODISSECTION SYSTEM

(71) Applicant: Leica Microsystems CMS GmbH, Wetzlar (DE)

(72) Inventors: Falk Schlaudraff, Butzbach/Nieder-Weisel (DE); Florian Hoffmann, Giessen (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 698 days.

(21) Appl. No.: 14/049,241

(22) Filed: Oct. 9, 2013

(65) Prior Publication Data

US 2014/0098214 A1    Apr. 10, 2014

(30) Foreign Application Priority Data

Oct. 9, 2012 (DE) ..................... 10 2012 218 382

(51) Int. Cl.
*G01N 33/483* (2006.01)
*G01N 1/28* (2006.01)

(52) U.S. Cl.
CPC ......... *G01N 33/483* (2013.01); *G01N 1/2813* (2013.01); *G01N 2001/282* (2013.01); *G01N 2001/2886* (2013.01)

(58) Field of Classification Search
CPC .................................................. G02B 21/367
USPC .......................................................... 348/79
See application file for complete search history.

(56) References Cited

U.S. PATENT DOCUMENTS

| 7,035,004 B2* | 4/2006 | Weiss .................... B23K 26/032 |
| | | 359/211.2 |
| 2002/0081014 A1 | 6/2002 | Ravkin |
| 2003/0021465 A1* | 1/2003 | Adel .................... G03F 7/70633 |
| | | 382/151 |
| 2004/0085443 A1 | 5/2004 | Kallioniemi et al. |
| 2004/0223215 A1 | 11/2004 | Weiss et al. |
| 2006/0186349 A1* | 8/2006 | Weiss ..................... G01N 1/286 |
| | | 250/486.1 |

(Continued)

FOREIGN PATENT DOCUMENTS

| AT | 505669 A4 | 3/2009 |
| DE | 10321091 B4 | 6/2005 |

(Continued)

*Primary Examiner* — Mohammed Rahaman
*Assistant Examiner* — Asmamaw G Tarko
(74) *Attorney, Agent, or Firm* — Leydig, Voit & Mayer, Ltd.

(57) ABSTRACT

A method for laser microdissection of a laser microdissection region of a prepared specimen includes driving a holder for the specimen into a holding position using a control device. First and second digital images are captured that depict a same portion of the prepared specimen, with the first image depicting the portion under at least one first microscopic examination method and the second image depicting the portion under at least a second microscopic examination method. A live overlay image is generated of the portion of the prepared image in a live mode. The live overlay is presented on a display area with the images overlaid onto one another. A marking is generated and captured on the live overlay image so as to define the laser microdissection region.

20 Claims, 2 Drawing Sheets

(56) References Cited

U.S. PATENT DOCUMENTS

| | | | |
|---|---|---|---|
| 2007/0066967 A1* | 3/2007 | Sieckmann | G01N 1/2813 606/10 |
| 2007/0105029 A1* | 5/2007 | Ausschnitt | B81C 99/0065 430/30 |
| 2008/0024766 A1* | 1/2008 | Mieher | G01N 21/956 356/73 |
| 2008/0194011 A1 | 8/2008 | Wesner | |
| 2009/0010900 A1* | 1/2009 | Fair | C12N 5/067 424/93.21 |
| 2009/0059094 A1* | 3/2009 | Yi | G09B 5/06 348/744 |
| 2010/0245557 A1* | 9/2010 | Luley, III | G02B 21/367 348/79 |
| 2011/0193024 A1* | 8/2011 | Wong | B82Y 30/00 252/301.4 P |
| 2011/0194749 A1 | 8/2011 | Morris | |
| 2012/0045790 A1* | 2/2012 | Van Dijk | G06T 7/0014 435/29 |
| 2012/0208184 A1* | 8/2012 | Ragan | G01N 1/06 435/6.11 |
| 2014/0011233 A1 | 1/2014 | Morimoto | |

FOREIGN PATENT DOCUMENTS

| | | |
|---|---|---|
| DE | 102005045165 B4 | 4/2008 |
| DE | 102005028062 B4 | 11/2010 |
| EP | 1846869 B1 | 10/2007 |
| EP | 2629078 A1 | 8/2013 |
| WO | WO 03105675 A2 | 12/2003 |
| WO | WO 2008080403 A1 | 7/2008 |
| WO | WO 2011149009 A1 | 12/2011 |

\* cited by examiner

Fig. 1

Fig. 2

METHOD FOR DEFINING A LASER MICRODISSECTION REGION, AND ASSOCIATED LASER MICRODISSECTION SYSTEM

CROSS REFERENCE TO RELATED APPLICATIONS

This application claims priority from German Patent Application No. 10 2012 218 382.5, filed Oct. 9, 2012, which is hereby incorporated by reference herein in its entirety.

FIELD

The present invention relates to a method for defining a laser microdissection region on a prepared specimen that is held by a holder of a laser microdissection system. An overlay image, in which a first digital image of a portion of the prepared specimen and a second digital image of the same portion are overlaid onto one another, is presented on a display area. On the overlay image, a marking is generated and captured in order to define the laser microdissection region. The invention further relates to a corresponding laser microdissection system, to a computer program having a program code for carrying out the method, and to a computer-readable storage medium for storing the computer program.

BACKGROUND

Laser microdissection is a method for cutting out ("dissecting"), with the aid of a focused laser beam, selected tissue regions or cells from microscope-examined tissue samples for further analysis. For this, microscopically examined regions of a prepared specimen are visualized on a display in computer-assisted fashion as a digital electronic image. Subregions that are to be analyzed are then marked in the electronic image and separated out.

US 2012/0045790 A1 relates to a variant of so-called "serial section cutting" (SSC). It describes a microdissection method in which a (first) image of a first sample section and a (second) image of a second sample section are generated. Based on a defined target region in the first image, a target region in the second image and in the corresponding second sample section is selected, which region is then cut out, for example, with a laser beam. Properties of two different sample sections are thus transferred in order to define a cut line. Overlaying of the two images ensures that the region of the first image matches that of the second image.

AT 505 669 A4 discloses a method in which a region to be investigated is determined by digital overlaying of an image of a first, untreated prepared section with an image of another, second, treated prepared specimen section from a section stack having multiple tissue sections located behind one another. The second prepared specimen section is adjacent to the first in the section stack and can be, for example, stained in such a way that specific structures can be recognized. The characteristics that were made visible with the aid of staining or other treatment of the adjacent section can be employed, by image overlaying, for selection of the dissection region on the untreated first section. The method thus makes possible dissection in which the dissectate remains untreated, and is thus available in its original state for further analysis.

Adjacent prepared specimen sections in a section stack are similar to one another, but usually not identical in terms of their structure. In addition, the treatment and viewing of different prepared specimen sections generally requires that an image of a first section be captured under a microscope and then removed from the microscope stage before the second prepared specimen section, which in turn must be placed at the identical position, can be viewed. This involves an increased outlay of time and work.

SUMMARY

In an embodiment, the present invention provides a method for laser microdissection of a laser microdissection region of a prepared specimen that is held by a holder of a laser microdissection system. The method includes driving the holder into a holding position using a control device of the laser microdissection system. A first digital image is captured that depicts a portion of the prepared specimen. The first digital image depicts the portion of the prepared specimen under at least one first microscopic examination method. At least one second digital image is captured of the same portion of the prepared specimen. The at least one second digital image depicts the portion of the prepared specimen under at least a second microscopic examination method. A live overlay image is generated of the same portion of the prepared image in a live mode. The live overlay is presented on a display area with the first digital image and at least one second digital image overlaid onto one another. A marking is generated and captured on the live overlay image so as to define the laser microdissection region.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

An aspect of the present invention is to reduce the outlay of time and work for selecting and marking a dissection region.

In an embodiment, the present invention is suitable for defining a laser microdissection region in a portion of a prepared specimen that is held by a holder of a laser microdissection system. The holder can be, for example, a microscope stage of a microscope by means of which a magnified image of a prepared specimen portion can be generated. For microscopic examination of a portion of the prepared specimen, according to the present invention a holding position of the holder is driven to by means of a control device of the laser microdissection system. The holding position is stationary relative to the optical axis of the light microscope, and in located in the field of view of the objective. The control unit can be operated, for example, by a user who is optically monitoring the respective microscopically examined region, or it can drive to predefined local coordinates. The method according to embodiments of the present invention furthermore encompasses capture of a first digital image that depicts a portion of the prepared specimen, capture of a second digital image of the same portion, and generation and presentation, on a display area, of an overlay image in which the first and the second digital image are overlaid onto one another.

The first digital image depicts the portion of the prepared specimen under at least one first microscopic examination method. The second digital image depicts the same portion of the prepared specimen under at least a second microscopic examination method different from the first one.

The first and second microscopic examination method(s) can each be defined, for example, by the use of a specific type of illumination (such as e.g. a specific illumination direction, incident or transmitted illumination, use of a selected light filter and/or of specific wavelengths), by one or more selected fluorescence excitation(s), by a contrasting method (such as e.g. a phase contrast method), or by a combination of the methods recited.

According to an embodiment of the present invention, a marking for definition of the laser microdissection region is generated on the overlay image and captured.

Preferably, the overlay image is a live image that is presented on a display area in "live" mode. A "live" image or an image presented in "live" mode is intended to be understood in the context of this application as an image, deposited in a working memory or a corresponding temporary memory, that can be immediately displayed and processed. Immediate full access, in particular including in real time, is thus possible. Conversely, this means that with the method according to the present invention it is possible to dispense with the use of an external image database or a corresponding nonvolatile memory and corresponding electronic image processing software, since only the images to be overlaid need to be temporarily stored for the method. All that is necessary is to implement an algorithm for image overlaying. Based on the live overlay image, a decision can be made immediately as to which region will be dissected. It is thus not necessary to store and then process large stacks of images in a nonvolatile memory; the need to travel back repeatedly to the same object region also does not exist. In addition, it is no longer necessary to generate images of a prepared specimen portion using two or more different microscopic examination methods and store them in stacked fashion. Instead, an instantaneous selection can be made, from the available microscopic examination methods, of two (or more) that are particularly suitable for selection and marking of a dissection region.

Based on a selected first microscopic examination method, a first digital image of a prepared specimen portion is therefore generated in live mode and temporarily stored. By means of a selected second microscopic examination method, a second digital image of the same portion is generated and is presented on a display area. The first and the (at least one) second digital image are then overlaid in a live overlay image. In live mode, a marking to define the laser microdissection region is then generated, and is captured for purposes of subsequent laser microdissection.

The laser microdissection method according to embodiments of the present invention thus operates in delay-free fashion and thus more quickly, moreover more economically and also more ergonomically for the user, since image overlaying can be performed in real time independently of further software modules, directly in the user program of the laser microdissection control software, after which the desired markings can be generated directly in the live overlay image with no need for image export and import processes for that purpose. The transfer or conversion of holding positions can also be omitted.

The live overlay image, which is produced preferably by a software program of the control device, can be generated, for example, with the aid of an addition of the pertinent pixel values, and exhibits specific features of both the first and the second digital image. Marking can therefore occur in consideration of those characteristics. The prepared specimen does not need to be moved or repositioned between capture of the second and of the first image (although this is not intended to be excluded). In particular, a second prepared specimen does not need to be put in place; the microscopic examination method simply needs to be changed. The method according to the present invention thus allows rapid and precise selection of a region to be dissected.

In a preferred embodiment, the holder is immobilized in the holding position before capture of the first digital image and/or of the (at least one) second digital image, and is kept immobilized until after capture of the marking or until after the laser microdissection region has been cut out. It is thereby possible to ensure, in simple and rapid fashion, that the portion of the prepared specimen is located at the same position upon capture of the first digital image as it is upon capture of the second digital image; that the two images can therefore be precisely overlaid; and/or that dissection occurs accurately in accordance with the marking.

In order to meet present-day requirements in terms of laser microdissection, it is useful if the images that are to be overlaid are overlaid in pixel-precise fashion. Pixel-precise overlaying can be achieved electronically and/or optically. Electronically, a corresponding image processing software program can perform a pixel-precise overlay of the images on the basis of identified image characteristics. On the other hand, it is possible in optical fashion to ensure that the images acquired using different microscopic examination methods are acquired with pixel-scale precision, i.e. not displaced with respect to one another, by an image sensor, so that subsequent electronic correction of any image shifts can in some circumstances be entirely omitted.

Optical "zero pixel shift" methods of this kind are described in, for example, from patents DE 103 21 091 B4 or DE 10 2005 045 165 B4, which are incorporated by reference herein in their entireties. According to DE 103 21 091 B4, the images to be overlaid are ones acquired by means of two microscopic examination methods, namely transmitted-light interference contrast microscopy (ICT) on the one hand, and fluorescence microscopy on the other hand. The polarizing filter used as an analyzer in the ICT method, which is removed from the beam path for fluorescence observation, causes a slight beam deflection of up to approximately 3 minutes. For example, if the microscope has a tube lens having a focal length of 200 mm, an analyzer of this kind generates an offset of up to 175 μm of the intermediate image of the sample. The consequence of this is in turn that in a CCD camera having a pixel size of approximately 8 μm, the image is offset approximately 20 pixels by the analyzer. To eliminate this pixel offset, this document proposes two glass wedge plates, which are arranged immediately behind the analyzer and are embodied and oriented in such a way that they compensate back to zero the beam deflection generated by the analyzer.

In the other patent document recited, DE 10 2005 045 165 B4, the beam offset generated by the blocking filter of a fluorescence cube is compensated for. The beam deflection here is only approximately 10", but can still cause an offset of approximately 1.5 pixels. In order to reduce the pixel offset to zero, this document proposes that the blocking filter substrate, i.e. the transparent substrate of the blocking filter on which a thin-layer system is implemented, be embodied as transparent wedge plates having wedge angles, and that they be aligned so that a minimized beam deflection, or none at all, with respect to the optical axis occurs. The same applies to the dichroic beam splitter present in a fluorescence cube, which (like the blocking filter) can generate a beam deflection.

Alternatively to the methods presented for pixel-precise overlaying, it is of course possible to determine the pixel shift that is caused by a specific microscopic examination method, and take it into account and compensate for it in the context of image overlaying.

The marking on the overlaid live image must ideally then be transferred in pixel-precise fashion onto the active live image, and the laser must be guided with pixel-scale precision along the marking. The overlaid images can of course be exported and stored in an image memory for later documentation purposes.

It can be useful if the first digital image is a depiction of the prepared specimen under the microscope at a first, earlier point in time, and the second digital image is a depiction of the prepared specimen under the microscope at a second, later point in time, but in particular at the current investigation point in time.

Capture of the first digital image can encompass importing the first digital image from an external storage medium into a calculation unit of the control device, the first digital image having been previously acquired and stored in the external memory medium. In this embodiment, importing the first digital image encompasses importing local coordinates with regard to acquisition of the first digital image, which preferably encompass local coordinates of the prepared specimen relative to the laser microdissection system in the context of the image acquisition that occurred at an earlier point in time. In this case, driving to the holding position occurs on the basis of the local coordinates.

An externally stored image can thereby be used as a first digital image. The control software preferably orients the laser microdissection system, on the basis of the imported local coordinates, in such a way that the prepared specimen is brought into the same position, relative to the laser microdissection system, in which the first digital image was acquired. This makes possible precise overlaying of the first and the second image, and/or accurate dissection in accordance with the marking (which includes along the marking).

The first digital image and the (at least one) second digital image can capture the same portion of the prepared specimen at the same magnification. The magnification is determined, in known fashion, by the microscope magnification of the microscope that is used for laser microdissection. Alternatively, however, it can also be advantageous if the first digital image and the (at least one) second digital image capture the same portion of the prepared specimen at different magnifications. The relevant portion of the prepared specimen is depicted, for example, in the first digital image in the form of an overview image that also depicts adjacent regions of the prepared specimen portion, while the second digital image, for example, depicts substantially only the relevant portion at high magnification. For generation of the live overlay image, the (at least one) digital image having the lower magnification is electronically zoomed to the higher magnification. Such a procedure makes it easier to localize the dissection region in an environment in which, for example, further dissection regions may be located.

The method preferably encompasses storing the first digital image and/or storing the second digital image and/or storing the overlay image and/or storing the local coordinates of the holding position. The corresponding data are thereby retained, and can be utilized, for example, in a subsequent analysis or for logging/documentation of a dissection process. In the case of storing the local coordinates of the holding position, once the marking is captured the prepared specimen can firstly be removed or brought into a different position (for example in order to mark another region of the prepared specimen), and later brought back into the holding position for dissection of the region. As a result, the steps of on the one hand marking multiple regions, and on the other hand dissecting the regions, can be separated from one another.

The method can encompass capture of a further digital image, where the further digital image depicts the portion of the prepared specimen under at least one further microscopic examination method that preferably is different from the first and second microscopic examination methods. The first digital image, the second digital image, and the further digital image can then be overlaid onto one another in the overlay image.

It is thus possible, for example in the context of marking, to incorporate data about the portion in the prepared specimen that can be made visible only by the use of three or more microscopic examination methods in succession.

The first digital image can in turn be an overlay image, which is referred to here for better differentiation as a "second overlay image." The overlay image mentioned above is then a first overlay image, in which the second overlay image (constituting the first digital image) and the second digital image are overlaid onto one another. The first overlay image can be generated, or can have been generated, from an overlay of a third digital image and a fourth digital image, in which context the third and the fourth digital image show the same portion of the prepared specimen as the second digital image but were generated under respective third and fourth microscopic examination methods that differ from one another and from the second microscopy method.

Analogously to the case described previously, it is thereby possible to incorporate additional information that can result from the third and fourth illumination types. In combination with the above-described embodiment in which the first digital image is imported into the calculation unit of the control device, the second overlay image can also have been generated and/or stored externally, for example with the aid of a special image processing software program.

The marking can, for example, be generated automatically with the aid of a pattern recognition software program, or can be inputted manually by a user. The display area can be, for example, a graphical user interface on which a user can carry out actions with the aid of an input means for a computer, for example positioning and moving a cursor or calling computer functions, and can thereby produce the marking.

The marking can be accomplished in accordance with selected, predefined specifications that, for example, define a specific shape of the marking (e.g. rectangle, square, ellipse, or circle). Marking is thereby made easier and thus faster.

The invention further relates to a laser microdissection system for executing the method according to embodiments of the present invention discussed above in detail. For this purpose, the laser microdissection system encompasses a holder for a prepared specimen, a control device for driving the holder into a holding position, a microscope for capturing a portion of the prepared specimen in the holding position of the prepared specimen holder under a first and at least one second microscopic examination method, and a digital image capture device for capturing a first and at least one second digital image respectively of the aforesaid prepared specimen portion. The system furthermore encompasses a laser device for dissecting a laser microdissection region by laser-cutting that region out of the prepared specimen portion along a predetermined marking. The digital image capture device comprises in this context a calculation unit, which is set up in such a way that the first and at least one second digital image are overlaid in live mode and are presented on a display area as a live overlay image, where the first digital image is generated under the aforementioned first microscopic examination method and the at least one second digital image is generated under the aforesaid at least one second microscopic examination method. Lastly, the laser microdissection system comprises a marking capture unit that captures a marking, generated on the live overlay image, for definition of the laser microdissection region within the prepared specimen portion. Dissection of the laser microdissection region is then accomplished by laser-cutting on the basis of this captured marking, the holder preferably remaining immobilized in the holding position during laser-cutting.

With regard to the advantages of the laser microdissection system according to the present invention, and of possible embodiments of that system, reference may be made to the entirety of the above explanations in connection with the method according to the present invention for laser microdissection. The digital image capture device of the laser microdissection system preferably encompasses a temporary memory for storing the first and/or the at least one second digital image as well as the overlay image. As already explained in detail above, the invention can dispense with bulk image memory (although this is not intended to be excluded). The calculation unit of the digital image capture device needs to comprise only an algorithm for image overlay. This algorithm can be, in particular, a constituent of the control software of the system which is already present. The temporary memory and the calculation unit of the image capture device can correspondingly be constituents of the control device. In addition, the aforesaid marking capture unit can be implemented in the control device.

It is understood that the features recited above and those yet to be explained below are usable not only in the respective combination indicated, but also in other combinations or in isolation, without departing from the scope of the present invention.

Figure 1:
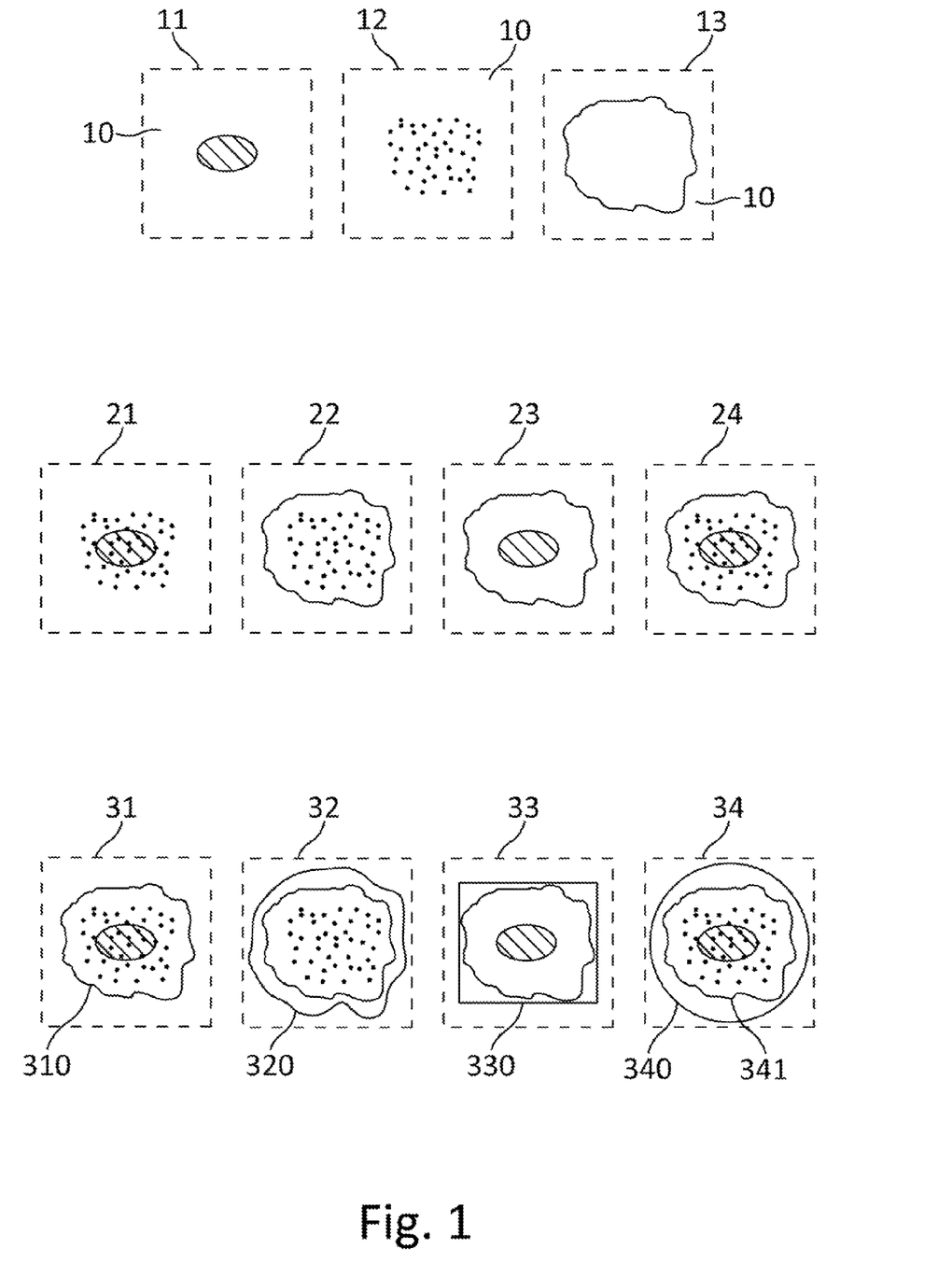
FIG. 1 schematically shows several digital images and overlays thereof.

FIG. 1 shows three digital images 11, 12, and 13 that depict a portion 10 of a prepared specimen (in this case a single cell) under different microscopic examination methods that each allow specific properties or details of the cell to be recognized.

Image 11 shows the cell as it appears with DAPI fluorescent staining as a first microscopic examination method. The cell nucleus is thereby recognizable, but the cell wall cannot be detected. The latter is visible in image 13, which was acquired using differential interference contrast (DIC) as a second microscopic examination method. In image 12, specifically marked organelles in the cell plasma were made visible using green fluorescence as a third microscopic examination method; in this image as well, the cell wall is not detectable. Each of the images 11, 12, and 13 can selectably be used as a first or second digital image in the terminology of the present application application, likewise as a third, fourth, or further digital image.

Images 21, 22, and 23 show overlay images each made up of two of the images 11, 12, and 13: in image 21, images 11 and 12 are overlaid onto one another; in image 22, images 12 and 13; and in image 23, images 11 and 13. Lastly, image 24 is an overlay image made up of all three images 11, 12, and 13 or made up of one of these images with an overlay image of the respective other two images. In the terminology of the present application application, for example, image 22 could be overlaid as a first digital image with image 11 as a second digital image.

In images 31 to 34, a marking was added on the respective overlay images 21 to 24 in order to define a laser microdissection region.

In image 31, marking line 310 was drawn automatically using image processing software after detection of the specimen contour, or manually using a suitable input device, for example a computer mouse or a pen on a touch-sensitive display on which image 21 is being displayed. With the aid of the marking added to overlay image 21, the cell nucleus together with the organelles can be dissected, for example if the cell wall is irrelevant for subsequent observation.

If, on the other hand, the cut is intended to dissect an entire cell that comprises the specifically stained organelles, it can be necessary to visualize a depiction of the cell wall. If information that can be obtained from staining of the cell nucleus is immaterial, it is appropriate to use overlay image 22. If, in addition to the organelles, information about the cell nucleus is also be utilized (for example if the only cells to be dissected and further investigated are ones whose nucleus exhibits specific properties), it may be advisable to use overlay image 24.

Images 32 and 34 correspondingly show respective markings 320 and 340 in the form of peripheral lines, which have been inserted respectively into overlay images 22 and 24. Marking line 320 was, for example, drawn by hand, for example with the aid of a computer mouse or with a pen on a touch-sensitive surface that is preferably the display area for the overlay image. Marking line 340, on the other hand, was drawn with the assistance of an automatic function that generates an ellipse. Advantageously, the latter can be suitably oriented, displaced, and/or adjusted in terms of axial ratio and/or size by drawing with an input means such as, for example, a computer mouse. Alternatively, marking line 340 can be generated automatically by image software in such a way that it encloses with minimum clearance the line 341 that represents the cell wall, and/or so that the ellipse has a minimum area. An axial ratio of the ellipse can be predetermined; in particular, it is possible to determine thereby that the ellipse is embodied as a circle.

In image 33, a rectangular marking line has analogously been inserted into overlay image 23. It, too, can be suitable aligned, displaced, and/or adjusted in terms of axial ratio and/or size by moving an input means, or it can be generated in optimized fashion via image software, for example, once a specific side ratio has been set.

Markings 310, 320, 330, and 340 can be respectively captured by the control software of the laser dissection system, and the dissection mechanism can be correspondingly controlled in such a way that the marked regions are cut out along the demarcation lines.

Figure 2:
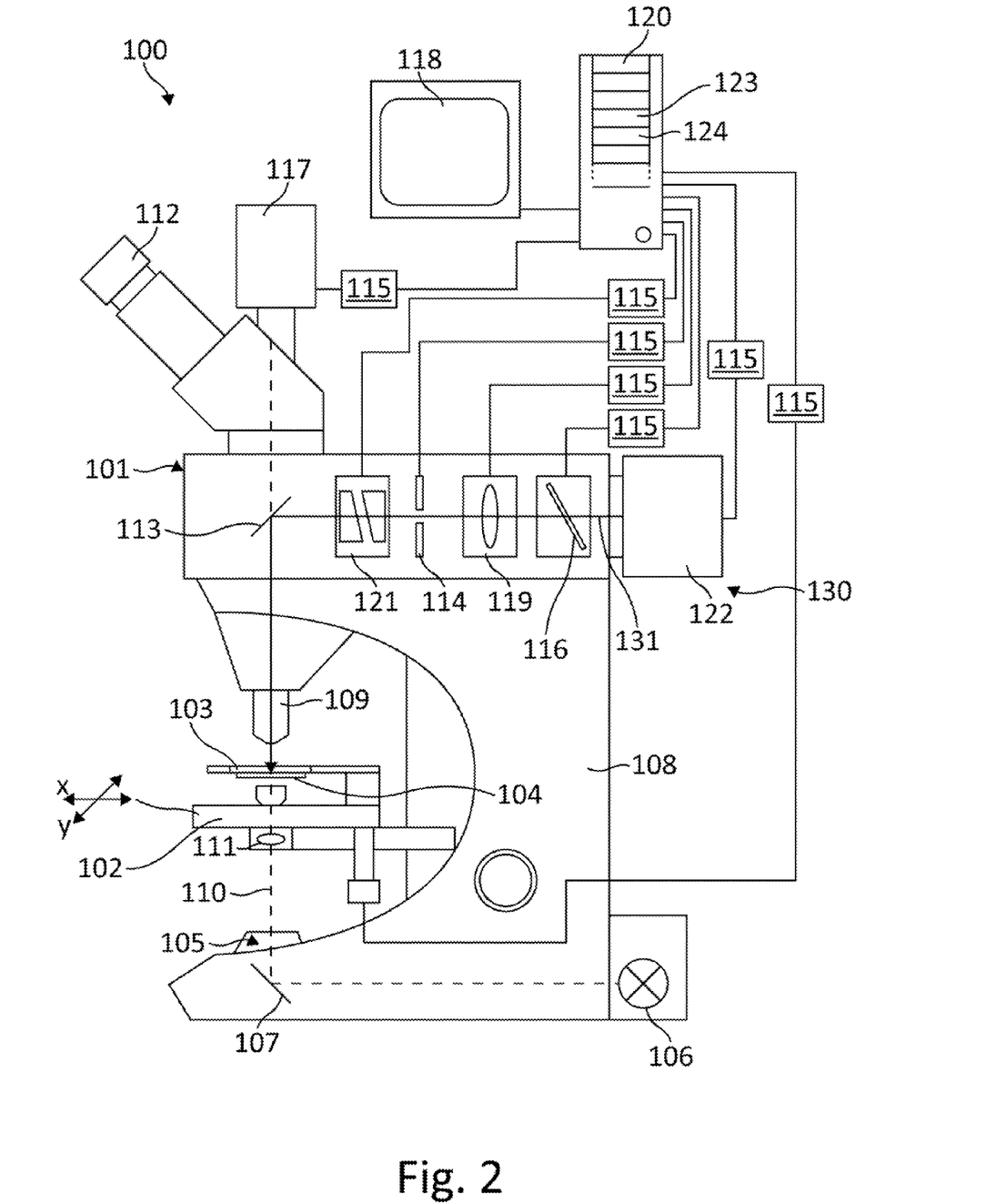
FIG. 2 is a schematic side view of a laser microdissection system.

FIG. 2 shows a laser microdissection system that can be used for the present invention. Laser microdissection systems are sufficiently known per se from the existing art. Reference may be made by way of example to a laser microdissection system such as the one described in detail in German patent DE 10 2005 028 062 B4. Reference will therefore be made expressly to this document with regard to specific details of this system that are mentioned hereinafter.

FIG. 2 is a schematic side view of a laser microdissection system 100 of this kind. This system 100 encompasses a microscope 101 having an X-Y stage that is displaceable in motorized fashion and serves to receive a sample holder 103 on which a prepared specimen 104 to be investigated and/or sectioned is placed. The number 105 designates in general an illumination system, in this case for transmitted illumination of prepared specimen 104. A light source 106, such as a halogen lamp or a white light LED, having a downstream illumination optic (not depicted in detail) for generating an illumination beam path, is provided for this. This illumination beam path is directed from below, by means of a deflection mirror 107 and a condenser 111, onto prepared specimen 104. Microscope 101 furthermore encompasses an objective 109 as well as microscope elements (not depicted in further detail) such as a zoom system, tube lenses, and eyepiece lenses.

Light passing through prepared specimen 104 travels to objective 109, which captures a portion of prepared specimen 104; a viewer can view a magnified image, corresponding to the respective microscopic examination method, of that portion through eyepiece 112. Microscope 101 is additionally connected to a camera 117 that can capture, for example via a CCD chip, a digital image of the prepared specimen portion. The image data acquired by camera 117 are conveyed to a computer 120 that is in turn connected to a display area 118 (here, a monitor) on which an image of the imaged prepared specimen portion can be presented. Although computer 120 and camera 117 are depicted separately in FIG. 2, the computer, in particular calculation unit 123, can also entirely or partly form one integral unit with the camera.

Laser microdissection system 100 that is depicted further encompasses a laser device 130 for dissecting a laser microdissection region by laser-cutting. For this, a laser 122 is coupled to microscope 101, for example by connecting laser 122 to microscope stand 108. Laser beam 131 generated by laser 122 is coupled via elements (yet to be explained) into optical axis 110 of microscope 101, and is focused onto prepared specimen 104 for cutting. By means of a relative motion between laser beam 131 and prepared specimen 104, the corresponding dissection region is then cut out of the prepared specimen along a predetermined marking (cut line). Whereas this relative motion can be implemented by corresponding motion of X-Y stage 102 and thus of holder 103 while laser beam 131 is stationary, it is preferred to move laser beam 131 while X-Y stage 102 and holder 103 are stationary during laser-cutting.

For this purpose, laser beam 131 is guided through an (optional) attenuator unit 116, a focusing optic 119, and an aperture unit 114. By means of these elements, a laser beam focus is generated in known fashion, with the desired intensity and geometry, at the desired site in prepared specimen 104. A deflection element 113 serves to couple laser beam 131 into optical axis 110 of microscope 101. A UV laser, for example, is suitable as laser 122.

The control device is labeled 115 in FIG. 2. It can encompasses units separate from one another, as depicted illustratively in FIG. 2, but in practice the control device as a rule represents a unit that can be integrated in particular, for example, into computer 120. In this exemplifying embodiment control device 115 is connected to laser 122, to attenuator unit 116, to focusing optic 119, to aperture unit 114, and to X-Y stage 102 so that these elements can be driven appropriately. A connection to camera 117 is also advisable, so that imaging parameters can be adjusted. Reference may be made to the previously mentioned DE 10 2005 028 062 B4 regarding further details.

A deflection unit 121 is arranged between aperture unit 114 and deflection element 113 in order to move the laser beam focus along a predetermined marking for dissection of a laser microdissection region, this deflection unit 121 in turn being connected to control device 115. This deflection unit 121 encompasses a wedge plate pair whose individual wedge plates can be oriented in modifiable fashion with respect to one another. The laser beam can thereby be deflected, in known fashion, out of the optical axis by an amount equal to an offset, so that it strikes prepared specimen 104 with a corresponding offset. It is thereby possible, by suitably driving deflection unit 121, to guide the laser beam focus along an arbitrarily predetermined marking or cut line.

Laser microdissection system 100 being discussed here allows capture of a prepared specimen portion, in particular in the context of an immobilized holding position of holder 103, under a first and at least a second microscopic examination method. Possible microscopic examination methods have already been variously addressed above. Only an illumination system 105 for transmitted illumination is depicted in FIG. 2. Elements necessary for other microscopic examination methods, for example for a contrasting method or an incident-light fluorescence method, are not depicted individually. Two different microscopic examination methods can, however, also be implemented using two different transmitted illumination types, for example transmitted bright-field and transmitted dark-field illumination. For this, the angle of incidence of the illumination beam path of illumination system 105 depicted here would need to be correspondingly adjusted.

A digital image capture device, which in the present case can be constituted by camera 117 and by calculation unit 123, captures a first and a second digital image of the same prepared specimen portion in each case, the two images being generated under different microscopic examination methods. Calculation unit 123 is set up in such a way that the first and the second digital image are overlaid in live mode, and are presented on display area 118 as a live overlay image. A viewer of display area 118 can thus, for example, view the relevant prepared sample portion under the various available microscopic examination methods. Examples of corresponding digital images were explained in detail in connection with FIG. 1. The viewer can then, for example, determine two (or three, or more) microscopic examination methods as being the most suitable for defining a dissection region. For that purpose he or she can, in particular, generate live overlay images and cause them to be presented in live mode on display area 118. Other microscopic examination methods may in turn be more suitable for a different prepared specimen or a different prepared specimen portion. The corresponding temporarily stored images are overlaid and presented on display area 118 as a live overlay image. The viewer can appropriately mark the laser microdissection region in this overlay image. Suitable marking means have already been discussed in detail in the description. A marking capture unit 124 captures the marking, for which purpose, for example, the marking is converted into a cut line along which laser beam 131 is then moved. Marking capture unit 124 is in this case a constituent of computer 120, with which, together with control device 115, deflection unit 121 is driven.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

PARTS LIST

10 Portion of a prepared specimen
11, 12, 13 First or second digital images
21, 22, 23, 24 Overlay images
32, 32, 33, 34 Overlay images with markings
310, 320, 330, 340 Markings
100 Laser microdissection system
101 Microscope
102 X-Y stage
103 Holder
104 Prepared specimen
105 Illumination system
106 Light source
107 Deflection mirror
108 Microscope stand
109 Objective
110 Optical axis
111 Condenser
112 Eyepiece
113 Deflection element
114 Aperture unit
115 Control device
116 Attenuator unit
117 Camera
118 Display area
119 Focusing optic
120 Computer
121 Deflection unit
122 Laser
123 Calculation unit
124 Marking capture unit
130 Laser device
131 Laser beam

What is claimed is:

1. A method for defining a laser microdissection region of a prepared specimen that is held by a holder of a laser microdissection system, the method comprising:

driving the holder into a holding position using a control device of the laser microdissection system;
capturing a first digital image that depicts a portion of the prepared specimen, the first digital image depicting the portion of the prepared specimen under at least one first microscopic examination method;
capturing a second digital image of the same portion of the prepared specimen, the second digital image depicting the portion of the prepared specimen under at least a second microscopic examination method;
generating a live overlay image of the same portion of the prepared specimen by overlaying the first digital image and the second digital image onto one another in a live mode;
presenting the live overlay image on a display area; and
generating and capturing a marking on the live overlay image so as to define the laser microdissection region.

2. The method according to claim 1, wherein the holder is immobilized in the holding position so as to retain the prepared specimen before the capturing the first digital image and kept immobilized in the holding position during the capturing the first digital image and the second digital image and until after the capturing the marking on the live overlay image.

3. The method according to claim 1, further comprising cutting out, by laser microdissection, the laser microdissection region in accordance with the marking on the live overlay image.

4. The method according to claim 3, wherein the holder is immobilized in the holding position so as to retain the prepared specimen before the capturing the first digital image and kept in the holding position during the capturing the first digital image and the second digital image and until after the cutting out, by laser microdissection, the laser microdissection region.

5. The method according to claim 1, wherein the first digital image and the second digital image are overlaid in pixel-precise fashion.

6. The method according to claim 1, wherein the first digital image and the second digital image capture the same portion of the prepared specimen at the same magnification.

7. The method according to claim 1, where the first digital image and the second digital image capture the same portion of the prepared specimen at different magnifications, and where for generation of the live overlay image, the one of the first digital image and the second digital image having, the lower magnification is electronically zoomed to the higher magnification.

8. The method according to claim 1, further comprising importing the first digital image into a calculation unit of the control device, the importing the first digital image including importing local coordinates of the prepared specimen relative to the laser microdissection system upon acquisition of the first digital image, and
wherein the holding position is driven to on the basis of the local coordinates.

9. The method according to one claim 1, further comprising at least one of:
storing the first digital image,
storing the at least one second digital image,
storing the overlay image, or
storing local coordinates of the holding position.

10. The method according to claim 1, further comprising capturing a further digital image,
wherein the further digital image depicts the portion of the prepared specimen under a further type of illumination, and wherein the first digital image, the second digital image, and the further digital image are overlaid onto one another in the overlay image.

11. The method according to claim 1, wherein the first digital image is a second overlay image in which a third digital image and a fourth digital image are overlaid onto one another, where the third and the fourth digital image depict the portion of the prepared specimen under different types of illumination.

12. A tangible non-transient computer-readable medium having computer-executable instructions stored thereon for defining a laser microdissection region of a prepared specimen that is held by a holder of a laser microdissection system, the computer-executable instructions including instructions for:
  driving the holder into a holding position using a control device of the laser microdissection system;
  capturing a first digital image that depicts a portion of the prepared specimen, the first digital image depicting the portion of the prepared specimen under at least one first microscopic examination method;
  capturing a second digital image of the same portion of the prepared specimen, the second digital image depicting the portion of the prepared specimen under at least a second microscopic examination method;
  generating a live overlay image of the same portion of the prepared specimen by overlaying the first digital image and the second digital image onto one another in a live mode;
  presenting the live overlay image on a display area; and
  generating and capturing a marking on the live image so as to define the laser microdissection region.

13. A laser microdissection system comprising:
  a holder for a prepared specimen;
  a control device for driving the holder into a holding position;
  a microscope for capturing a portion of the prepared specimen in the holding position under a first and at least one second microscopic examination method;
  a digital image capture device for capturing a first and a second digital image of the prepared specimen portion, the first digital image being generated under the first microscopic examination method, and the second digital image being generated under the at least one second microscopic examination method, the digital image capture device including a calculation unit configured so as to overlay the first and the second digital images in a live mode and present the overlaid first and second digital images on a display area as a live overlay image;
  a marking capture unit configured to capture a marking, generated on the live overlay image, for defining the laser microdissection region within the prepared specimen portion; and
  a laser device configured to dissect a laser microdissection region by laser-cutting the region out of the prepared specimen portion along the marking.

14. The laser microdissection system according to claim 13, wherein the digital image capture device includes a temporary memory for storing the first and/or the second digital image, as well as the overlay image.

15. The laser microdissection system according to claim 14, wherein the temporary memory and the calculation unit of the image capture device and/or the marking capture unit is each a constituent of the control device and/or of an associated computer.

16. The method according to claim 1, wherein the portion of the prepared specimen is located at the same position for the capturing of the first digital image as for the capturing of the second digital image.

17. The tangible non-transient computer-readable medium of claim 12, wherein the holder is immobilized in the holding position before the first digital image and/or the second digital image is captured, and the holder is kept immobilized until after capture of t:he marking.

18. The tangible non-transient computer-readable medium of claim 12, wherein the portion of the prepared specimen is located at the same position for the capturing of the first digital image as for the capturing of the second digital image.

19. The laser microdissection system according to claim 13, wherein the control device and the holder are configured to hold the portion of the prepared specimen at the same position for the capturing of the first digital image as for the capturing of the second digital image.

20. The laser microdissection system according to claim 13, wherein the control device is configured to immobilize the holder in the holding position so as to retain the prepared specimen before the first digital image is captured and to retain the holder in the holding position during the capture of the first digital image and the second digital image and until after the cutting out, by laser microdissection, the laser microdissection region.

* * * * *